United States Patent [19]

Chen et al.

[11] Patent Number: 5,059,724

[45] Date of Patent: Oct. 22, 1991

[54] PREPARATION OF METHYL ISOBUTYL KETONE

[75] Inventors: Po Y. Chen, Tao Yuan; Shiao J. Chu; Cha C. Chen, both of Hsin Chu; Nan S. Chang, Tai-nan; Wen C. Lin; T. K. Chuang, both of Hsin Chu, all of Taiwan

[73] Assignee: Industrial Technology Research Institute, Hsinchu, Taiwan

[21] Appl. No.: 531,395

[22] Filed: May 31, 1990

Related U.S. Application Data

[63] Continuation-in-part of Ser. No. 240,316, Sep. 2, 1988, abandoned.

[51] Int. Cl.$^5$ .............................................. C07C 45/45
[52] U.S. Cl. ..................................................... 568/396
[58] Field of Search ........................................ 568/396

[56] References Cited

U.S. PATENT DOCUMENTS

| | | | |
|---|---|---|---|
| 3,574,763 | 4/1971 | Wallner et al. | 568/396 |
| 3,953,517 | 4/1976 | Schmitt et al. | 568/396 |
| 4,270,006 | 5/1981 | Heilin et al. | 568/396 |
| 4,339,606 | 7/1982 | Huang et al. | 568/396 |
| 4,701,562 | 10/1987 | Olson | 568/396 |
| 4,866,210 | 9/1989 | Hoilderich et al. | 568/396 |

*Primary Examiner*—James H. Reamer
*Attorney, Agent, or Firm*—Darby & Darby

[57] ABSTRACT

Process for selective synthesis of methyl isobutyl ketone by reacting in vapor phase or vapor/liquid phase acetone and hydrogen, e.g. in 0.5–3:1 molar ratio at 150°–300° C. and 1–30 atm., in the presence of a modified palladium-containing ZSM-5 zeolite catalyst, e.g. of 0.05–5% Pd content, as porous crystalline aluminosilicate catalyst having a 15–700:1 silica to alumina ratio, e.g. at a weight hourly space velocity of 0.5–8 hr$^{-1}$, the catalyst being prepared by treating a completely acidic ZSM-5 zeolite sequentially with alkali metal cations and palladium ions and then activating the resultant zeolite in a reducing atmosphere.

4 Claims, No Drawings

PREPARATION OF METHYL ISOBUTYL KETONE

RELATED APPLICATION

This application is a continuation-in-part of copending U.S. patent application Ser. No. 240,316, filed Sept. 2, 1988 now abandoned.

FIELD AND BACKGROUND OF THE INVENTION

In the prior art, methyl isobutyl ketone (MIBK) has been produced in a three-stage process, by aldol condensation of acetone to form diacetone alcohol which is catalyzed by a base, dehydration of that alcohol to mesityl oxide with an acid catalyst, and hydrogenation of that unsaturated ketone to MIBK with nickel or copper chromite catalyst (Kudo, S., "Formation of Higher Molecular Weight Ketones from Acetone or Isopropanol," J. Chem. Soc. Japan, Ind. Chem. Sect., 58 (1955), 785787; Showa Denkc, "Production of Methyl Isobutyl Ketone from Acetone," Japanese 46-2009 (Jan. 19, 1971); and Minoda, S., et al., "Acetone Purification," French 1,535).

MIBK has also been synthesized from hydrogen and acetone in one step under high pressure in the presence of a palladium-containing cation exchange resin catalyst. Disadvantages of this Pd-resin catalyst process are the short life of the catalyst, the problem of its regeneration due to the thermal instability of the resin (i.e. an organic polymer) at temperatures above 160° C. and its tendency for inducing polymer formation, plus the high cost of the required high pressure system and its complicated operation ("New Solvent Process," Ind. Research (July 1968), 25-26; and Takagi, K., et al., "Methyl Isobutyl Ketone," German 1,936,203 (Feb. 12, 1970)).

Japan Kokkai 73/16492 describes a process in which MIBK was obtained in a yield of only 13.4% by vapor phase reaction of acetone with hydrogen at 250° C. using a 0.01-2.00% Pd-containing 13X zeolite catalyst.

German Offen. 3,021,764 discloses a process for preparing MIBK with a 36% yield using a transition metal complex catalyst, but at a high pressure of 180 atm. It has the disadvantages of high pressure operation, and the difficulties of separating the products from the homogeneous catalyst.

U.S. Pat. No. 4,801,752, issued Jan. 31, 1989, of common assignee herewith, discloses a process for selective production of N-alkyl and N,N-dialkylaniline by reacting in vapor phase aniline with an alkanol having 1—3 carbon atoms, e.g. methanol, at 300°-500° C. and 1-5 atm. pressure, in the presence of a crystalline aluminosilicate catalyst having a silica to alumina ratio of 20-700:1, which may be modified with alkali metal, alkali earth metal or transition metal ions, such as a ZSM-5 zeolite containing sodium or hydrogen cations impregnated or ion-exchanged with cesium, magnesium, ferric or potassium ions (Chen, P. Y., et al., "The Selective Alkylation of Aniline With Methanol Over ZSM-5 Zeolite," Chem. Abst., July 6, 1987, vol. 107:6705h).

DESCRIPTION OF THE INVENTION

This invention relates to a one-step process for selective production of methyl isobutyl ketone directly from hydrogen and acetone in the presence of a palladium-containing ZSM-5 series zeolite catalyst comprising a porous crystalline aluminosilicate of high silica to alumina ratio, i.e. from about 15:1 to 700:1, preferably about 30:1 to 100:1. The Pd-containing ZSM-5 zeolite catalysts may be modified by Pd impregnation and by ion exchange with hydrogen, alkali metal and transition metal, e.g. Pd, cations.

The process of the invention is highly selective for forming MIBK, suppressing formation of such unwanted by-products as diisobutyl ketone (formed by trimeric condensation of acetone), light hydrocarbons and isopropanol, and can be carried out continuously and in the vapor phase or vapor/liquid phase at low temperature, and especially at low pressure.

As compared to said conventional Pd-resin catalyst process, by using a highly active ZSM-5 zeolite catalyst according to the invention, MIBK can be prepared in a continuous process at from about ordinary pressure, i.e. 1 atm., to about 30 atm., taking advantage of the high thermal stability of the ZSM-5 zeolite, which is attributed to its compositions of inorganic oxides. The instant catalyst modification permits suitable adjustment of the pore size and acidity of the ZSM-5 zeolite for achieving high activity and selective production of MIBK. Such modified zeolites advantageously possess weak acid strength and enough Pd metal active sites to perform as an efficient bifunctional catalyst for MIBK synthesis.

Yields of MIBK as high as 30%, e.g. based on a high selectivity of 82% of 42% converted acetone, are obtained by the instant one-step synthesis at ordinary pressure, and use of Pd-containing ZSM-5 zeolite as solid catalyst eliminates the problems of separating the reaction products from the catalyst.

This invention advantageously provides a process using a highly thermostable catalyst for preparing MIBK, while avoiding the drawbacks of high pressure and thermally unstable resin-supported catalysts associated with conventional processes.

Table 1A sets forth advantages of this invention in using the Pd-containing ZSM-5 zeolite catalyst as compared with the conventional Pd-containing resin catalyst for producing MIBK.

TABLE 1A

| | Catalyst | |
|---|---|---|
| Characteristics | Pd-containing ZSM-5 zeolite | Pd-containing Resin |
| Thermal stability of support | Good | Destroyed by heat |
| Catalyst regeneration | Easy | Difficult |
| High pressure equipment | Not required | Required |
| Reaction type | Vapor phase/ Vapor-liquid phase | Vapor-liquid phase |

The zeolite ZSM-5 used in this invention is a crystalline aluminosilicate zeolite having a composition in terms of mole ratios of oxides as follows:

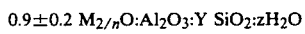

wherein M is at least one cation having a valence n, Y is at least about 15, and z is between 0 and 40. This zeolite is further characterized by a specified X-ray diffraction pattern shown below in Table 1B:

TABLE 1B

| Interplanar Spacing d(A): | Relative Intensity |
|---|---|
| 11.1 ± 0.2 | s. |
| 10.0 ± 0.2 | s. |
| 7.4 ± 0.15 | w. |
| 7.1 ± 0.15 | w. |

TABLE 1B-continued

| Interplanar Spacing d(A): | Relative Intensity |
| --- | --- |
| 6.3 ± 0.1 | w. |
| 6.04 ± 0.1 | w. |
| 5.97 | |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

These values are determined by standard techniques. The radiation is the K-alpha doublet of copper, and a scintillation counter spectrometer with a strip chart pen recorder is used. The peak heights, I, and the positions as a function of 2 times theta, where theta is the Bragg angle, are read from the spectrometer chart. From these, the relative intensities, 100 $I/I_o$, where $I_o$ is the intensity of the strongest line or peak, and d (obs.), the interplanar spacing in A, corresponding to the recorded lines, are calculated. In Table 1B the relative intensities are given in terms of the symbols s.=strong, w.=weak and v.s.=very strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it had been subjected to thermal treatment. (See U.S. Pat. No. 4,082,085.)

The zeolite ZSM-5, depending on the $SiO_2$ to $Al_2O_3$ ratio, has a surface area of from 250 to 450 $m^2/g$ and a pore volume of from 0.15 to 0.35 $cm^2/g$. Its Constraint Index is 8.3. (See U.S. Pat. No. 4,350,835.) Zeolite ZSM-5 and its preparation are more particularly described in U.S. Pat. No. 3,702,886.

In the instant MIBK synthesis, acetone may be pumped, vaporized, mixed with hydrogen, preheated, and then introduced into a fixed-bed reactor and contacted with the catalyst at a temperature of at least about 150° C., such as about 150° to 300° C., preferably about 200° to 250° C., and a pressure of at most about 30 atmospheres, such as about 1 to 30 atmospheres.

The molar ratio of hydrogen to acetone is about 0.5:1 to 3.0:1, preferably about 1:1 to 3:1, and the weight hourly space velocity or WHSV (grams of acetone feed per gram of catalyst per hour) is about 0.5 to 8 $hr^{-1}$, preferably about 1 to 8 $hr^{-1}$, and more preferably about 1 to 2 $hr^{-1}$.

The ZSM-5 zeolites are conventionally obtained by crystallization in sodium form, designated NaZSM-5 zeolite. NaZSM-5 zeolite is synthesized under the conditions in which water is present in considerable amount and frequently at elevated temperatures. For example, the crystallization may be effected by hydrothermal process, i.e. autoclaving at 160°–180° C. for 0.5 to 15 days until crystallization is complete, followed by filtering, washing, drying and calcining in a stream of air at 550° C. for 6–24 hours. This procedure is described in U.S. Pat. No. 3,702,886.

By ion-exchange processing, the sodium cations in the synthesized and calcined NaZSM-5 may be exchanged with hydrogen ions, with ammonium salts (e.g., $NH_4Cl$ or $NH_4NO_3$) or with mineral acid (e.g., $NHO_3$ or HCl) to form zeolites having hydrogen cations, designated HZSM-5, following by filtering, washing and calcining in air.

HZSM-5 zeolite may be treated by ion exchange, e.g. with 0.1M sodium, cesium, potassium, etc., nitrate solution at 80° C., repeatedly until optimum exchange capacity is reached. The ion exchange product, designated NaHZSM-5, CsHZSM-5, KHZSM-5, etc., zeolite, is then filtered, washed and dried.

NaHZSM-5, CsHZSM-5, KHZSM-5, etc. may be ion-exchanged or impregnated with palladium cations, e.g. as a water-soluble Pd salt solution such as a nitrate, acetate or chloride, to form Pd-impregnated zeolites, designated Pd/NaZSM-5, Pd/HZSM-5, Pd/NaHZSM-5, Pd/CsHZSM-5, Pd/KHZSM-5, etc. Generally, such ZSM-5 zeolite is soaked in the impregnating solution overnight, then dried and calcined at 550° C. for 12–24 hours.

The palladium content in the catalyst is from about 0.05 to 5% by weight, preferably about 0.06 to 1.0% by weight, and more preferably about 0.5 to 1.0% by weight.

In the ion exchange process, the Pd or other metal ions enter the zeolite pore channels and exchange with hydrogen ions. In the impregnation process, the Pd ions remain on the zeolite outer surface and are converted to the metal oxide during calcining. Both of these processes change the intrinsic properties of ZSM-5 zeolite.

Apart from Pd, the elements used for catalyst modification herein are the alkali metals such as Li, Na, K, Rb and Cs, and the other transition metals such as Fe, Co, Ni; Ru, Rh; and Os, Ir, Pt; plus Cu. The highest activity can be achieved by ion exchange of the ZSM-5 zeolite with an alkali metal cation, followed by impregnation with palladium.

Hydrogen, or a mixture of hydrogen and nitrogen, is employed to activate (reduce) the catalyst, at temperatures from 300° to 500° C. for about 2 to 8 hours.

The following examples are merely illustrative of preferred embodiments of the invention. Many variations thereon may be made without departing from the spirit of the disclosed invention, as will be evident to those skilled in the art, and such variations are intended to come within the scope of what is claimed.

EXAMPLE 1

The procedure disclosed in U.S. Pat. No. 3,702,886 was adapted for the synthesis of zeolites having various $SiO_2/AlO_3$ ratios. Aluminum sulfate (up to 20 g) in aqueous solution was added to an aqueous solution of water glass (180–280 g) and tetrapropylammonium bromide (10–50 g) to provide a silica to alumina molar ratio of from 30:1 to 680:1 (based on about 1–24 minimoles of aluminum sulfate and about 0.96–1.5 moles of silica in water glass). However, basicity was adjusted by adding sulfuric acid. This was followed by a hydrothermal process to obtain the product, i.e. the solution was agitated for 3 hours and then crystallized by autoclaving at 160° C. for 16 hours, and the formed NaHZSM-5 zeolite filtered, washed, dried and calcined in air at 550° C. for 16 hours.

To form HZSM-5 zeolite, the NaHZSM-5 zeolite was ion exchanged with H+ cations by treating with aqueous ammonium nitrate, filtering, washing, drying at 110° C. and calcining in air at 550° C. for 3 hours.

HZSM-5 zeolite was ion exchanged with 0.1M alkali nitrate solution, such as cesium nitrate solution, repeatedly in the same way to form the corresponding metal cation containing HZSM-5 zeolite.

In general, various ion exchange modified forms, designated mHZSM-5 zeolites (where m stands for alkali or transition metal ion), such as CsHZSM-5, KHZSM-5, PdHZSM-5 and CuHZSM-5 zeolites, were obtained by ion exchange of HZSM-5 zeolite with an appropriate solution concentration (0.01–0.1M) of water soluble alkali or transition metal salt, such as nitrates, acetates and chlorides of Cs, K, Pd, Cu, etc.

Pd/mHZSM-5 zeolites were obtained by soaking mHZSM-5 zeolite overnight with the $Pd(NH_4)Cl_2$ impregnating solution for providing the appropriate Pd loading amount, followed by drying, and calcining in air at 550° C. for 12–24 hours, the Pd wt. % of the impregnated product being based on the mHZSM-5 zeolite.

Each of the prepared Pd-containing ZSM-5 zeolite catalysts was treated (reduced) with hydrogen at 300°–500° C. for 2–8 hours for activation, while disposed as a fixed bed (1.7 g of 12–20 mesh catalyst) in a ⅜" cylindrical reactor. The temperature was then reduced to the operating temperature, acetone was pumped in, vaporized, mixed with hydrogen and thereafter contacted with the given catalyst. After reaction, the reactor effluent was cooled and collected by condensation in a cold trap at the reactor bottom, and the collected liquid products analyzed by gas chromatography.

The unreacted acetone may be recovered from the reaction products and advantageously recycled.

EXAMPLE 2

Per Example 1, catalysts were used which were prepared by appropriate treatment of the ZSM-5 zeolite, and these were compared with other catalysts as to activity. Table 2 shows that the catalysts of the invention provide excellent MIBK selectivity. All runs were effected as follows:

Reaction: Temperature 250° C.; pressure 1 atm.; WHSV 2 $hr^{-1}$; $H_2$ to acetone molar ratio 1:1.

Catalyst: 1% by wt. Pd; silica to alumina molar ratio 30:1; activation with $H_2$ at 400° C. for 8 hours before use:

TABLE 2

| Comparative Catalyst Activity | | |
|---|---|---|
| Catalyst | Acetone Conversion (%) | MIBK Selectivity (%) |
| Invention: | | |
| Pd/NaHZSM-5 zeolite* | 41.0 | 71.3 |
| PdHZSM-5 zeolite** | 22.6 | 82.3 |
| Other #: | | |
| Pd/Z-13X zeolite | 36.9 | 39.8 |
| Pd/Z-Y zeolite | 14.4 | 20.8 |
| Pd/Z-B zeolite | 22.6 | 27.0 |
| Pd/$Al_2O_3$ | 77.9 | 23.8 |
| Pd/$SiO_2$ | 15.1 | 29.1 |
| Pd/$TiO_2$ | 13.2 | 46.2 |

*Prepared by Pd impregnation of NaHZSM-5 zeolite.
**Prepared by ion exchange of HZSM-5 zeolite with Pd cation.
Each of these six catalysts was prepared by Pd impregnation of the corresponding zeolite, alumina ($Al_2O_3$), silica ($SiO_2$) or titania ($TiO_2$) as support. The Z-13X and Z-Y zeolites are from Linde Division, Union Carbide Corp., and Z-B zeolite is prepared according to U.S. Pat. 3,308,069.

The above data show the outstanding combination of acetone conversion and MIBK selectivity obtained by using the Pd/NaHZSm-5 zeolite of the invention.

Though the selectivity obtained with the Pd/HZSM-5 zeolite is high, the conversion is extremely poor. Furthermore, the other catalysts illustrated show very low selectivity to MIBK.

EXAMPLE 3

Per Example 1, catalysts were used which were prepared with and without ion exchange metal modification of the ZSM-5 zeolite. Table 3 shows that such modification enhanced conversion and MIBK selectivity. All runs were effected as follows:

Reaction: Temperature 250° C.; pressure 1 atm.; WHSV 2 $hr^{-1}$; $H_2$ to acetone molar ratio 1:1.

Catalyst: 1% by wt. Pd, with and without ion exchange metal modification of ZSM-5 zeolite; silica to alumina molar ratio 30:1; activation with $H_2$ at 400° C. for 8 hours before use:

TABLE 3

| Activity With and Without Modifying Ion Exchange | | |
|---|---|---|
| Catalyst | Acetone Conversion (%) | MIBK Selectivity (%) |
| Pd/HZSM-5 | 27.6 | 64.7 |
| Pd/NaHZSM-5 | 41.0 | 71.3 |
| Pd/KHZSM-5 | 45.3 | 67.8 |
| PD/CsHZSM-5 | 41.9 | 82.4 |

The above table clearly shows that the alkali metal ion exchanged zeolites of the invention give superior conversion, compared to the first zeolite described in the above table, while maintaining high selectivity.

EXAMPLE 4

Per Example 1, catalysts were used which were prepared with different silica to alumina ratios of the ZSM-5 zeolite. Table 4 shows that in general conversion and MIBK selectivity increased with decreasing ratio (increasing alumina content). All runs were effected as follows:

Reaction: Temperature 250° C.; pressure 1 atm.; WHSV 2 $hr^{-1}$; $H_2$ to acetone molar ratio 1:1.

Catalyst: 1% by wt. Pd; silica to alumina molar ratio 30:1 to 680:1; activation with $H_2$ at 400° C. for 8 hours before use:

TABLE 4

| Activity At Different Silica to Alumina Ratios | | |
|---|---|---|
| Catalyst # | Acetone Conversion (%) | MIBK Selectivity (%) |
| Pd/NaHZSM-5 (30) | 41.0 | 71.3 |
| Pd/NaHZSM-5 (100) | 35.8 | 62.0 |
| Pd/NaHZSM-5 (255) | 5.8 | 11.1 |
| Pd/NaHZSM-5 (680) | 12.8 | 4.8 |

The $SiO_2/Al_2O_3$ molar ratio of the silica-alumina used to prepare the catalyst is shown in parentheses.

EXAMPLE 5

Per Example 1, catalysts were used which were prepared with different Pd weight % of the ZSM-5 zeolite. Table 5 shows high conversion and high MIBK selectivity throughout the range. All runs were effected as follows:

Reaction: Temperature 250° C.; pressure 1 atm.; WHSV 2 $hr^{-1}$; $H_2$ to acetone molar ratio 1:1.

Catalyst: 0.1 to 1% by wt. Pd; silica to alumina molar ratio 30:1; activation with $H_2$ at 400° C. for 8 hours before use:

TABLE 5

Activity At Different Pd Weight %

| Catalyst | Acetone Conversion (%) | MIBK Selectivity (%) |
|---|---|---|
| 1.0 wt. % Pd/NaHZSM-5 | 41.0 | 71.3 |
| 0.7 wt. % Pd/NaHZSM-5 | 53.3 | 62.3 |
| 0.5 wt. % Pd/NaHZSM-5 | 46.1 | 56.4 |
| 0.2 wt. % Pd/NaHZSM-5 | 31.9 | 66.2 |
| 0.1 wt. % Pd/NaHZSM-5 | 33.1 | 78.9 |

EXAMPLE 6

Per Example 1, 0.7 wt. % Pd/NaHZSM-5 zeolite was prepared and used as catalyst at different reaction temperatures. Table 6 shows 200°–250° C. to be optimum for high MIBK selectivity while avoiding coking. All runs were effected as follows:

Reaction: Temperature 150° to 300° C.; pressure 1 atm.; WHSV 2 hr$^{-1}$; $H_2$ to acetone molar ratio 1:1.
Catalyst: 0.7% by wt. Pd/NaHZSM-5; silica to alumina molar ratio 30:1; activation with $H_2$ at 400° C. for 8 hours before use:

TABLE 6

Activity At Different Temperatures

| Temperature (°C.) | Acetone Conversion (%) | MIBK Selectivity (%) |
|---|---|---|
| 150 | 35.90 | 12.20 |
| 200 | 48.10 | 38.10 |
| 250 | 45.60 | 63.10 |
| 300 | 27.50 | 25.80 |

EXAMPLE 7

Per Example 1. 0.7 wt. % Pd/NaHZSM-5 zeolite was prepared and used as catalyst at different space velocities (WHSV). Table 7 shows optimum performance at lower space velocities. All runs were effected as follows:

Reaction: Temperature 250° to 300° C.: pressure 1 atm.; WHSV 1 to 8 hr$^{-1}$; $H_2$ to acetone molar ratio 1:1.
Catalyst: 0.7% by wt. Pd/NaHZSM-5; silica to alumina molar ratio 30:1; activation with $H_2$ at 400° C. for 8 hours before use:

TABLE 7

Activity At Different Space Velocities

| WHSV (hr$^{-1}$) | Temperature (°C.) | Acetone Conversion (%) | MIBK Selectivity (%) |
|---|---|---|---|
| 1 | 250 | 62.40 | 55.40 |
| 1.35 | 250 | 51.00 | 58.80 |
| 2 | 250 | 43.90 | 64.80 |
| 3 | 250 | 30.10 | 63.80 |
| 8 | 300 | 10.30 | 54.90 |

EXAMPLE 8

Per Example 1. 0.7 wt. % Pd/NaHZSM-5 zeolite was prepared and used as catalyst at different hydrogen to acetone molar ratios. Table 8 shows optimum performance at leaner hydrogen levels. All runs were effected as follows:

Reaction: Temperature 250° C.; pressure 1 atm.; WHSV 2 hr$^{-1}$; $H_2$ to acetone molar ratio 0.5:1 to 3:1.
Catalyst: 0.7% by wt. Pd/NaHZSM-5; silica to alumina molar ratio 30:1; activation with $H_2$ at 400° C. for 8 hours before use:

TABLE 8

Activity At Different Hydrogen/Acetone Molar Ratios

| Hydrogen to Acetone Molar Ratio | Acetone Conversion (%) | MIBK Selectivity (%) |
|---|---|---|
| 0.5 | 29.80 | 66.60 |
| 1 | 45.60 | 63.10 |
| 2 | 55.90 | 46.70 |
| 3 | 61.60 | 37.90 |

EXAMPLE 9

Per Example 1, catalysts were prepared with different Pd weight % of the ZSM-5 zeolite and used at different reaction pressures at constant temperature. Table 9 shows the versatility of the instant process. All runs were effected as follows:

Reaction: Temperature 200° C.; pressure 1 or 28.6 atm.; WHSV 1.6 or 2 hr$^{-1}$; $H_2$ to acetone molar ratio 0.63:1 or 1:1.
Catalyst: 0.7% and 0.3% by wt. Pd/NaHZSM-5; silica to alumina molar ratio 30:1; activation with $H_2$ at 400° C. for 8 hours before use:

TABLE 9

Activity At Different Reaction Pressure

| Catalyst | Reaction Pressure (atm.) | $H_2$ to Acetone Molar Ratio | WHSV (hr$^{-1}$) | Acetone Conversion (%) | MIBK Selectivity (%) |
|---|---|---|---|---|---|
| 0.7 wt. % Pd/NaHZSM-5 | 1 | 1 | 2 | 48.10 | 38.10 |
| 0.3 wt. % Pd/NaHZSM-5 | 28.6 | 0.63 | 1.6 | 67.02 | 63.83 |

EXAMPLE 10

Per Example 1, 0.7 wt. % Pd/NaHZSM-5 zeolite was prepared and activated at different periods of time and temperatures, and used as catalyst. Table 10 shows the suitability of all such conditions. All runs were effected as follows:

Reaction: Temperature 250° C.; pressure 1 atm.; WHSV 2 hr$^{-1}$; $H_2$ to acetone molar ratio 1:1.
Catalyst: 0.7% by wt. Pd/NaHZSM-5; silica to alumina molar ratio 30:1; activation with $H_2$ at 300° to 500° C. for 2 to 8 hours before use:

TABLE 10

Activation At Different Temperatures and Time

| Activating Temperature (°C.) | Activating Time (hrs) | Acetone Conversion (%) | MIBK Selectivity (%) |
|---|---|---|---|
| 300 | 8 | 46.40 | 64.70 |
| 400 | 8 | 46.90 | 64.80 |
| 500 | 8 | 41.00 | 67.60 |
| 400 | 4 | 41.70 | 64.10 |
| 400 | 2 | 42.90 | 62.60 |

What is claimed is:
1. A process for the selective production of methyl isobutyl ketone, which comprises reacting in the vapor phase or the vapor/liquid phase acetone and hydrogen at a temperature of about 150° to 300° C. and a pressure of about 1 to 30 atmospheres, in the presence of a ZSM-5 zeolite catalyst having a molar ratio of from $SiO_2/Al_2O_3$ of about 30:1 to 100:1 and about 0.05 to 1% by weight of palladium, wherein said catalyst is prepared by treating a substantially completely acidic ZSM-5 zeolite with an alkali metal ion, m, so as to form a zeolite having the formula mHZSM-5, adding palladium to said mHZSM-5 zeolite by impregnation or ion-exchange, and activating the resulting catalyst with hydrogen or a mixture of hydrogen and nitrogen for at least two hours.

2. The process of claim 1 wherein said alkali metal ion is sodium, potassium or cesium.

3. The process of claim 1 wherein the palladium is added to the catalyst by impregnation.

4. The process of claim 1 wherein the acidified ZSM-5 catalyst is prepared by ion-exchanging the sodium form of the ZSM-5 zeolite.

* * * * *